United States Patent
Shiomi et al.

(10) Patent No.: US 6,876,964 B1
(45) Date of Patent: Apr. 5, 2005

(54) APPARATUS FOR DETECTING FATIGUE AND DOZE BY VOICE, AND RECORDING MEDIUM

(75) Inventors: Kakuichi Shiomi, 5-13, Fujimoto 1-chome, Kokubunji-shi, Tokyo (JP); Shozo Hirose, Osaka (JP)

(73) Assignees: Electronic Navigation Research Institute, Independent Administrative Institution, Tokyo (JP); Osaka Gas Information System Research Institute Co., Ltd., Osaka (JP); Kakuichi Shiomi, Tokyo (JP)

( * ) Notice: Subject to any disclaimer, the term of this patent is extended or adjusted under 35 U.S.C. 154(b) by 492 days.

(21) Appl. No.: 09/691,126

(22) Filed: Oct. 19, 2000

(30) Foreign Application Priority Data

Oct. 5, 1998 (JP) .......................................... 10-283098

(51) Int. Cl.[7] .............................................. G10L 21/00
(52) U.S. Cl. ...................... 704/202; 704/270; 704/274
(58) Field of Search .............................. 704/202, 231, 704/270, 274

(56) References Cited

U.S. PATENT DOCUMENTS

| | | | | |
|---|---|---|---|---|
| 4,984,276 A | * | 1/1991 | Smith | 381/63 |
| 5,404,422 A | * | 4/1995 | Sakamoto et al. | 704/232 |
| 5,473,694 A | * | 12/1995 | Carroll et al. | 380/263 |
| 5,664,578 A | * | 9/1997 | Boczan | 600/549 |
| 5,689,241 A | * | 11/1997 | Clarke et al. | 340/575 |
| 5,800,265 A | * | 9/1998 | Yamazaki et al. | 463/23 |
| 5,813,989 A | * | 9/1998 | Saitoh et al. | 600/484 |
| 5,853,005 A | * | 12/1998 | Scanlon | 600/459 |
| 6,236,968 B1 | * | 5/2001 | Kanevsky et al. | 704/275 |
| 6,313,749 B1 | * | 11/2001 | Horne et al. | 340/575 |
| 6,400,310 B1 | * | 6/2002 | Byrnes et al. | 342/115 |
| 6,547,746 B1 | * | 4/2003 | Marino | 600/554 |
| 6,594,524 B2 | * | 7/2003 | Esteller et al. | 607/45 |

FOREIGN PATENT DOCUMENTS

| | | |
|---|---|---|
| JP | 4-208136 | 7/1992 |
| JP | 7-116119 | 5/1995 |
| JP | 7-117595 | 5/1995 |
| JP | 9-308614 | 12/1997 |
| JP | 2000-113347 | 4/2000 |

* cited by examiner

*Primary Examiner*—Vijay Chawan
*Assistant Examiner*—Michael N. Opsasnick
(74) *Attorney, Agent, or Firm*—Birch, Stewart, Kolasch & Birch, LLP (57) ABSTRACT

An apparatus for judging a fatigue level and/or a dozing state of a person by capturing voices uttered at different points of time from a microphone 5M. A computer performs chaos analysis of the digital data of the inputted voices and calculates Lyapunov exponents and judges a fatigue level and/or a dozing state based on the result of the chaos analysis.

6 Claims, 5 Drawing Sheets

| PC13: TO REMOVE A VOICELESS PART FROM DATA |
|---|
| PC14: TO GENERATE DATA, IF NECESSARY |
| PC15: TO CALCULATE LYAPUNOV EXPONENTS BY CHAOS ANALYSIS OF DIGITAL DATA (CHAOS ANALYSIS PROCESS) |
| PC16: TO STORE CALCULATION RESULTS OF LYAPUNOV EXPONENTS IN HDD 13 OR RAM 18 |
| PC17: TO READ LYAPUNOV EXPONENTS STORED IN HDD 13 OR RAM 18 |
| PC18: TO DETERMINE FATIGUE LEVEL AND/OR DOZING STATE BY COMPARING LYAPUNOV EXPONENTS OF VOICES UTTERED AT DIFFERENT POINTS OF TIME |
| PC19: TO GIVE ALARM ACCORDING TO RESULT OF DETERMINATION |

FIG. 5

ABSTRACT TEXT

APPARATUS FOR DETECTING FATIGUE AND DOZE BY VOICE, AND RECORDING MEDIUM

BACKGROUND OF THE INVENTION

The present invention relates to an apparatus for detecting a fatigue level of a person and detecting whether the person is in a drowsy state and in a state of doze (hereinafter these states are both referred to as a "dozing state") by analyzing voice, more specifically the person's speaking voice, and also relates to a recording medium on which a program for realizing such an apparatus with a general-purpose computer is recorded.

There have been instances of serious accidents caused by airplane pilots, air traffic controllers or drivers of public transport systems, such as trains, taxies, tracks and buses, who were dozing or in an extremely fatigued state, and there have also been many instances of various accidents, though they did not develop into serious accidents, in which such a doze or extremely fatigued state was a contributing factor. Conventionally, for example, whether a pilot, air traffic controller or driver is in such a state is judged by his/her superior's observation during the morning roll call, but the observation by human's eyes has its limitation and there is also a high possibility that his/her state will change thereafter.

In resent years, however, not only in the aviation field, but also in the public transport systems as mentioned above, it is possible to readily communicate with a driver by radio communication and to presume the driver's fatigue level to a certain extent from the tone of his/her voice during the communication. Moreover, there is such a system that it regards no communications over a certain period of time as a high possibility of occurrence of some abnormality, and provide sa warning. However, it is difficult in practice for a person to judge another person's fatigue level or judge accurately whether another person is in a dozing state by listening the speaking voice of another person.

In view of such circumstances, nowadays, for instance, there have been thoughts that the physical conditions, for example, the states of pulse and pupil, of a driver are detected with a sensor and transmitted for analysis by radio with the use of radio traffic facilities introduced in various public transport systems as mentioned above.

For example, Japanese Patent Application Laid-Open No. 9-308614 (1997) discloses a technique of knowing a person's mental and physical conditions from the pulse wave and electrocardiogram, and Japanese Patent Application Laid-Open No. 7-117595 (1995) discloses a technique of detecting a doze from the pulse wave. Further, in resent years, chaos analysis has been often used as a technique of analyzing the obtained data. For instance, Japanese Patent Application Laid-Open No. 4-208136 (1992) discloses a technique of detecting a person's health level, fatigue level and state of doze by chaos analysis of the person's pulse wave. In addition, Japanese Patent Application Laid-Open No. 7-116119 (1995) discloses a technique of judging a person's health level by chaos analysis of the area of pupil and the refractive index of the lens of the person's eye.

However, with the techniques based on the pulse wave, electrocardiogram, the area of pupil and the refractive index of the lens as mentioned above, it is necessary to attach some sensor to a person as a subject and to send the information obtained by the sensor by radio or cable, or to analyze the information on the spot by an analyzer. Moreover, in the case where a sensor is attached to a person's body, the person may fall into unusual mental and physical conditions due to the stress caused by the attachment of the sensor. In this case, the information about the person in normal conditions, which is to be used as criteria for judgment, can not be obtained, and thus there is a fear that accurate detection and judgment are not performed.

By the way, the inventors of this application calculated the Lyapunov exponents by chaos analysis of voices uttered by a person, compared the calculation results in a time series, and gained knowledge that the Lyapunov exponents are higher when the person's fatigue level is high or when the person falls into a doze. Accordingly, by calculating the Lyapunov exponents of voices uttered by a person at different points of time and comparing them, it is possible to detect the person's fatigue level and/or dozing state.

BRIEF SUMMARY OF THE INVENTION

The present invention was made in view of such circumstances, and its object is to provide an apparatus for detecting fatigue and doze by voice, which is capable of making accurate judgment by performing chaos analysis of voice uttered during communications by a person having an occupation in which the person nowadays performs radio communications daily, such as a driver of various public transport systems and of course an airplane pilot and an air traffic controller, and thereby readily obtaining information about the person in normal conditions, without attaching to the person as a subject a special sensor in addition to a device such as a headset which has been conventionally used to conduct his/her task.

Another object is to provide an apparatus for detecting fatigue and doze by voice, which is capable of making accurate detection irrespective of the languages or words spoken by a subject's voice.

A further object of the present invention is to provide a recording medium on which a program capable of realizing an apparatus as mentioned above with a general-purpose computer is recorded.

An apparatus of the first invention for detecting fatigue and doze by voice characterized by comprising a controller capable of performing the following operations: calculating Lyapunov exponents by chaos analysis of digital data of voices; and judging a fatigue level and/or a dozing state by comparing the calculated Lyapunov exponents of voices uttered at different points of time.

An apparatus of the second invention for detecting fatigue and doze by voice characterized by further comprising, in addition to the first invention, a microphone for inputting a voice as a sound signal; and an analog/digital converting device for converting the sound signal inputted to the microphone into digital data.

An apparatus for detecting fatigue and doze by voice char of the third invention characterized in that, in the first invention, the calculation of the Lyapunov exponents by the controller is performed by chaos analysis of digital data of sound signals recorded on a recording medium.

An apparatus of the fourth invention for detecting fatigue and doze by voice characterized in that, in the first invention, the controller is further capable of performing the operation of removing a voiceless part from the digital data prior to the calculation of the Lyapunov exponents.

An apparatus of the fifth invention for detecting fatigue and doze by voice characterized in that, in the fourth invention, the controller is further capable of performing the operation of generating digital data of a predetermined length by data based on the digital data, in the case where a data length of the digital data after removing the voiceless part is less than the predetermined length, prior to the calculation of the Lyapunov exponents.

An apparatus of the sixth invention for detecting fatigue and doze by voice characterized by further comprising, in addition to the first invention, a storing device for storing calculation results obtained by the operation of calculating the Lyapunov exponents, and wherein the controller is coupled to the storing device and further capable of performing the operation of comparing the Lyapunov exponents of voices uttered at different points of time, based on the calculation results which were obtained in advance by the operation of calculating the Lyaputiov exponents and are stored in the storing device, during the judging operation.

A computer readable recording medium of the seventh invention on which a program for causing a computer to detect a fatigue level and/or a dozing state by analysis of voices uttered at different points of time is recorded, characterized by including: program code means for causing a computer to calculate Lyapunov exponents by chaos analysis of digital data of voices; and program code means for causing a computer to judge a fatigue level and/or a dozing state by comparing the Lyapunov exponents of the voices uttered at different points of time.

A recording medium of the eighth invention characterized by further including, in addition to the seventh invention, program code means for causing a computer to remove a voiceless part from loaded digital data.

A recording medium of the ninth invention characterized by further including, in addition to the seventh invention, program code means for causing a computer to generate digital data of a predetermined length from data based on the loaded digital data, in the case where a data length after removing the voiceless part from the loaded digital data is less than the predetermined length.

A recording medium of the tenth invention characterized by further including, in addition to the seventh invention; program code means for causing a computer to store calculation results of the Lyapunov exponents; program code means for causing a computer to read the stored Lyapunov exponents; and program code means for causing a computer to compare the read Lyapunov exponents of voices uttered at different points of time.

A computer readable recording medium of the eleventh invention on which a program for causing a computer to detect a fatigue level and/or a dozing state by analysis of voices uttered at different points of time is recorded, characterized by including: program code means for causing a computer to remove a voiceless part from digital data of voices; program code means for causing a computer to generate digital data of a predetermined length from data based on loaded digital data, in the case where a data length after removing a voiceless part from the loaded digital data is less than the predetermined length; program code means for causing a computer to give the loaded data to a chaos analyzing process for calculating Lyapunov exponents by chaos analysis; program code means for causing a computer to store calculation results of the Lyapunov exponents calculated by the chaos analyzing process; program code means for causing a computer to read the stored Lyapunov exponents; and program code means for causing the computer to judge a fatigue level and/or a dozing state by comparing the read Lyapunov exponents of voices uttered at different points of time.

According to the first and second inventions, since the Lyapunov exponent is calculated by chaos analysis of the digital data of an inputted voice, it is possible to judge a person's fatigue level and/or dozing state by comparing the Lyapunov exponents calculated from voices uttered by the person at different points of time. This will be explained more specifically below.

Figure 1:
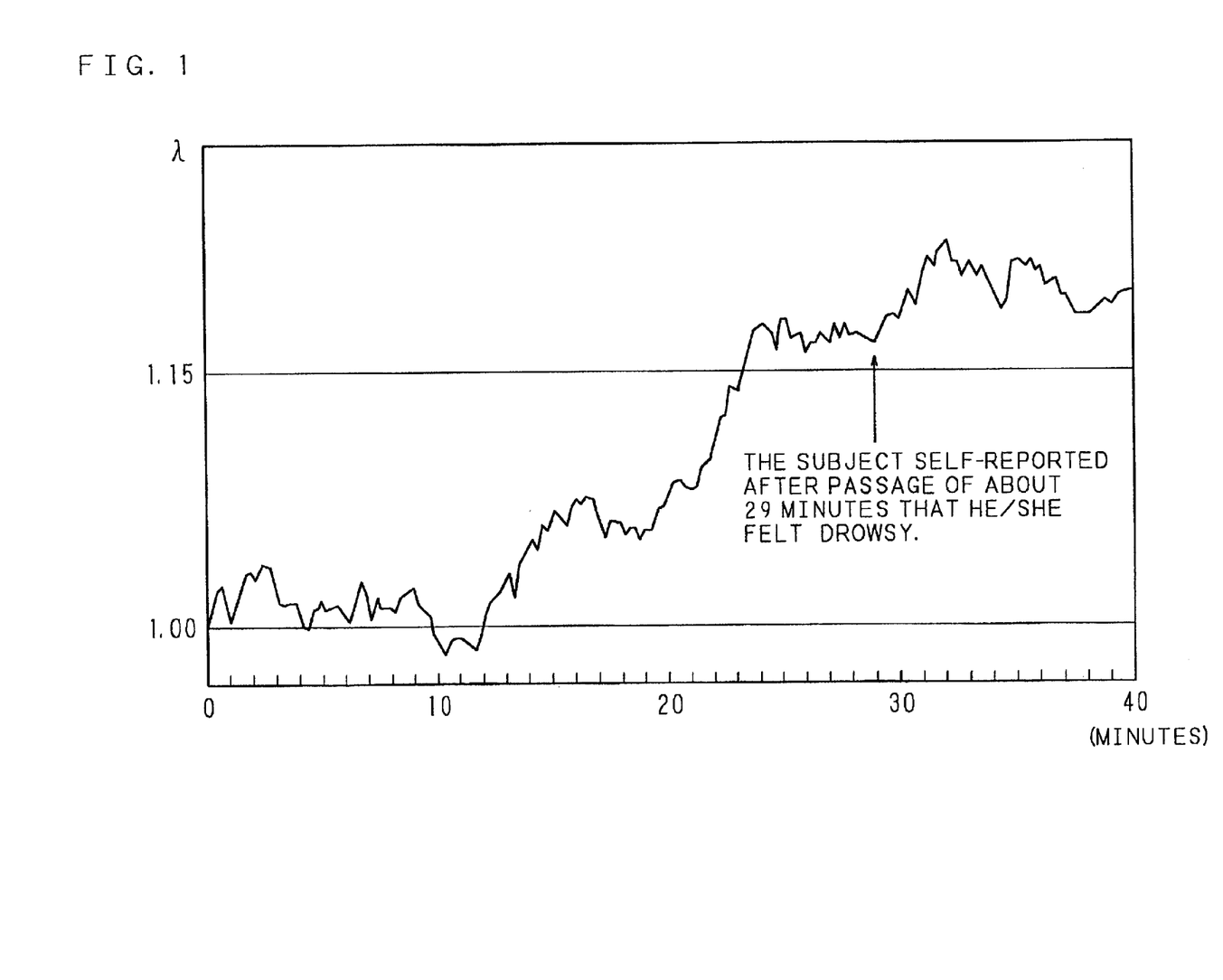
FIG. 1 is a graph of the time-series data of the Lyapunov exponents showing the principle of an apparatus for detecting fatigue and doze by voice of the present invention.

FIG. 1 is a graph showing the results of an experiment performed by the inventors of this application, and the experiment was carried out under the following conditions. A phrase of about two to three seconds was sampled from a voice uttered by one person as the subject, continuously for 40 minutes at a rate of about 10 data per minute, and the Lyapunov exponents $\lambda$ of the respective data were calculated. Note that in the graph of FIG. 1, moving averages of the data in the past five minutes are shown by relative values with respect to the value (416) of the Lyapunov exponent $\lambda$ at the start time of the experiment as "1.00". The subject self-reported at the start time of the experiment that he/she did not feel drowsy nor fatigued, but self-reported after the passage of about 29 minutes from the start time of the experiment that he/she felt drowsy.

It would be appreciated from the results of the experiment that the Lyapunov exponent $\lambda$ increased to about 1.17 in the relative value at the time when about 29 minutes passed from the start time of the experiment, at which the subject self-reported that he/she felt drowsy. More specifically, the Lyapunov exponent $\lambda$ did not show a significant change for about 10 minutes from the start time of the experiment, but the Lyapunov exponent $\lambda$ started to show a significant increasing tendency from a time in the vicinity of the passage of 10 minutes and the subject self-reported that he/she felt drowsy after the relative value became more than about 1.15 at a time in the vicinity of the passage of 23 minutes.

The inventors of this application gained knowledge from the above-mentioned results of the experiment that the subject can be judged as in a state in which the subject's fatigue accumulated to a certain extent or in a dozing state when the Lyapunov exponent becomes more than about 1.15 in the relative value which is "1.00" at the start time of the experiment and this state continues for a while thereafter. Moreover, the inventors of this application gained knowledge that the subject can be judged as in a state in which the subject's fatigue accumulated to a certain extent or in a dozing state when the increasing rate of the Lyapunov exponent reaches or exceeds a certain value.

According to the second invention, since the voice of a person as a subject is inputted from a microphone and converted into digital data, if, for example, a microphone of a headset which is used daily by, particularly, a airplane pilot, air traffic controller, a driver of public transport systems and so on is used, the person as the subject of detection does not have to bear any burden.

According to the third invention, since the Lyapunov exponent calculating means performs chaos analysis of the digital data of a sound signal recorded on a recording medium, in the case where the voice is kept recorded on the recording medium, it can be analyzed afterward.

According to the fourth and eighth inventions, a voiceless part is removed from the digital data and then only the data necessary for analysis is inputted.

According to the fifth and ninth inventions, even when the data length after removing a voiceless part from the digital data is less than a predetermined length necessary for analysis, data with a data length necessary and sufficient for analysis is inputted.

According to the sixth and tenth inventions, by storing the Lyapunov exponents obtained in a time series from the same person in storing means, it is possible to detect the person's state of fatigue and/or dozing which changes with the passage of time. Moreover, by storing the Lyapunov exponents, which were obtained as the result of analysis of the voices of a plurality of persons in normal conditions in advance, as the reference values of the respective persons in the storing means, it is possible to perform prompt and accurate detection on a number of persons as the subjects.

According to the eleventh invention, when a program for performing only chaos analysis is separately prepared, the use of the program makes it possible to realize an apparatus for detecting fatigue and doze by voice of the present invention with a general-purpose computer.

The above and further objects and features of the invention will more fully be apparent from the following detailed description with accompanying drawings.

DETAILED DESCRIPTION OF THE INVENTION

Figure 2:
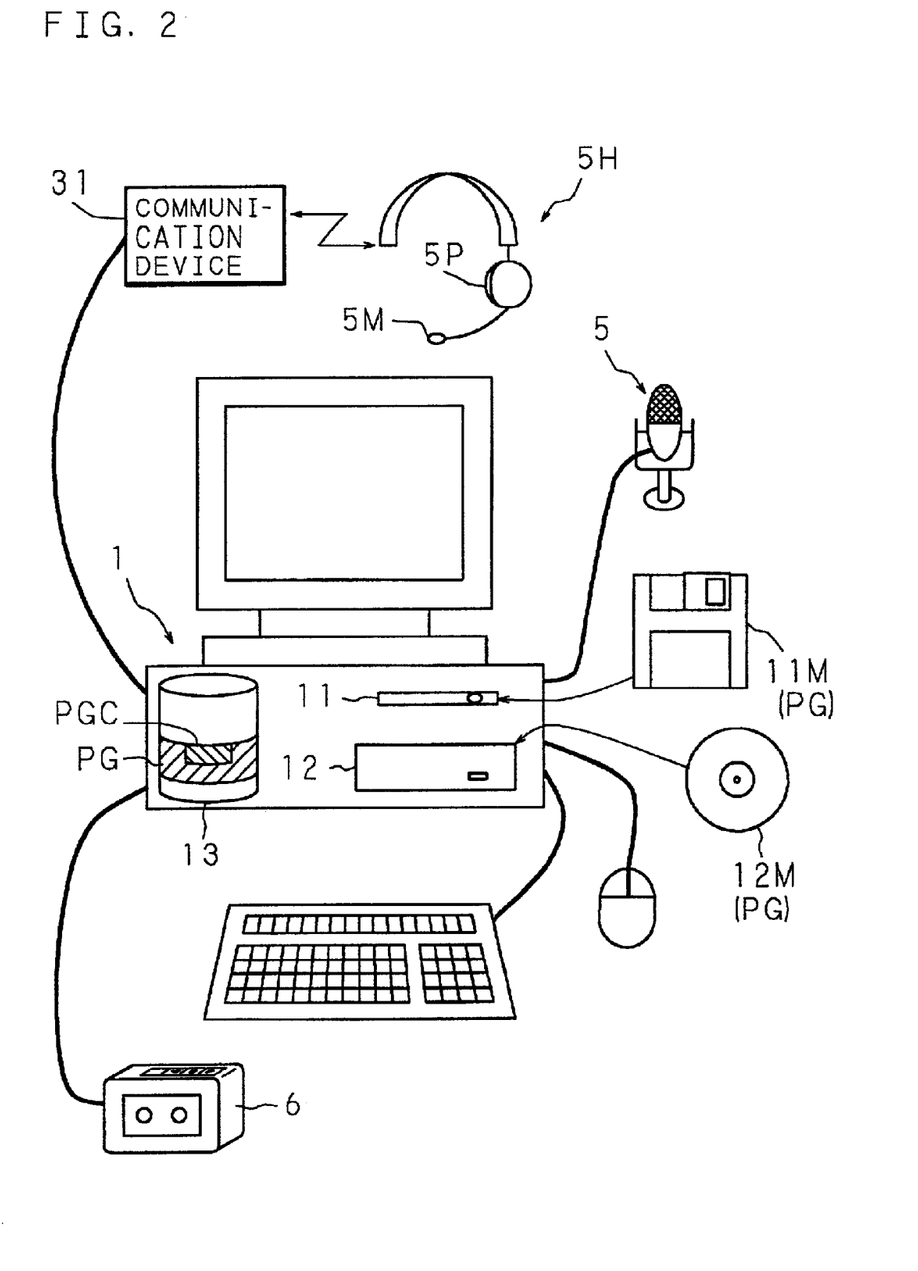
FIG. 2 is a schematic drawing showing an example of the entire constitution of an apparatus for detecting fatigue and doze by voice of the present invention, which is realized by the use of a personal computer.

The present invention will be described in detail below with reference to the drawings illustrating an embodiment thereof. FIG. 2 is a schematic drawing showing an example of the entire constitution of an apparatus for detecting fatigue and doze by voice according to the present invention (hereinafter referred to as the "apparatus of the present invention"), which is realized by the use of a computer.

In FIG. 2, reference numeral 1 represents a personal computer provided with a flexible disk drive (FDD) 11 and a CD-ROM drive (CDD) 12 for reading the recorded contents (program codes) from a flexible disk 11M or CD-ROM 12M on which a program PG for detecting fatigue and doze (hereinafter referred to as the "doze detecting program") is recorded. However, needless to say, it is also possible to use various types of recording media other than the flexible disk 11M and CD-ROM 12M.

The personal computer 1 also includes therein a hard disk drive (HDD) 13 as non-volatile storing means which stores the respective program codes of the doze detecting program PG read from the above-mentioned flexible disk 11M or CD-ROM 12M. Besides, the doze detecting program PG includes a chaos analyzing program PGC. This chaos analyzing program PGC is a program for calculating the Lyapunov exponent by chaos analysis of the digital data of a voice loaded by the doze detecting program PG.

Moreover, a microphone 5 and a communication device 31 are directly connected to the personal computer 1. In addition, a CRT display, a keyboard and mouse functioning as inputting means and a pointing device, etc. are connected to the personal computer 1. Further, a headset 5H including a headphone 5P and a microphone 5M is connected to the communication device 31 by cable or radio communication.

Incidentally, the microphone 5 is used in such a case where the voices of a number of persons in normal conditions are sampled in advance. Besides, the microphone 5M of the headset 5H is worn by a person as a subject (hereinafter referred to as the "subject") of detection of a fatigue level or a dozing state by the apparatus of the present invention in normal working conditions, and is used for capturing the voice of the person wearing the headset 5H as a sound signal in real time.

Furthermore, a voice reproducing device, for example, a tape recorder 6, capable of recording sound signals on a recording medium and reproducing and outputting the sound signals is connectable to the personal computer 1. This tape recorder 6 is used when analyzing the sound signals recorded on an audio tape as the recording medium afterward for some reasons by the apparatus of the present invention.

Figure 3:
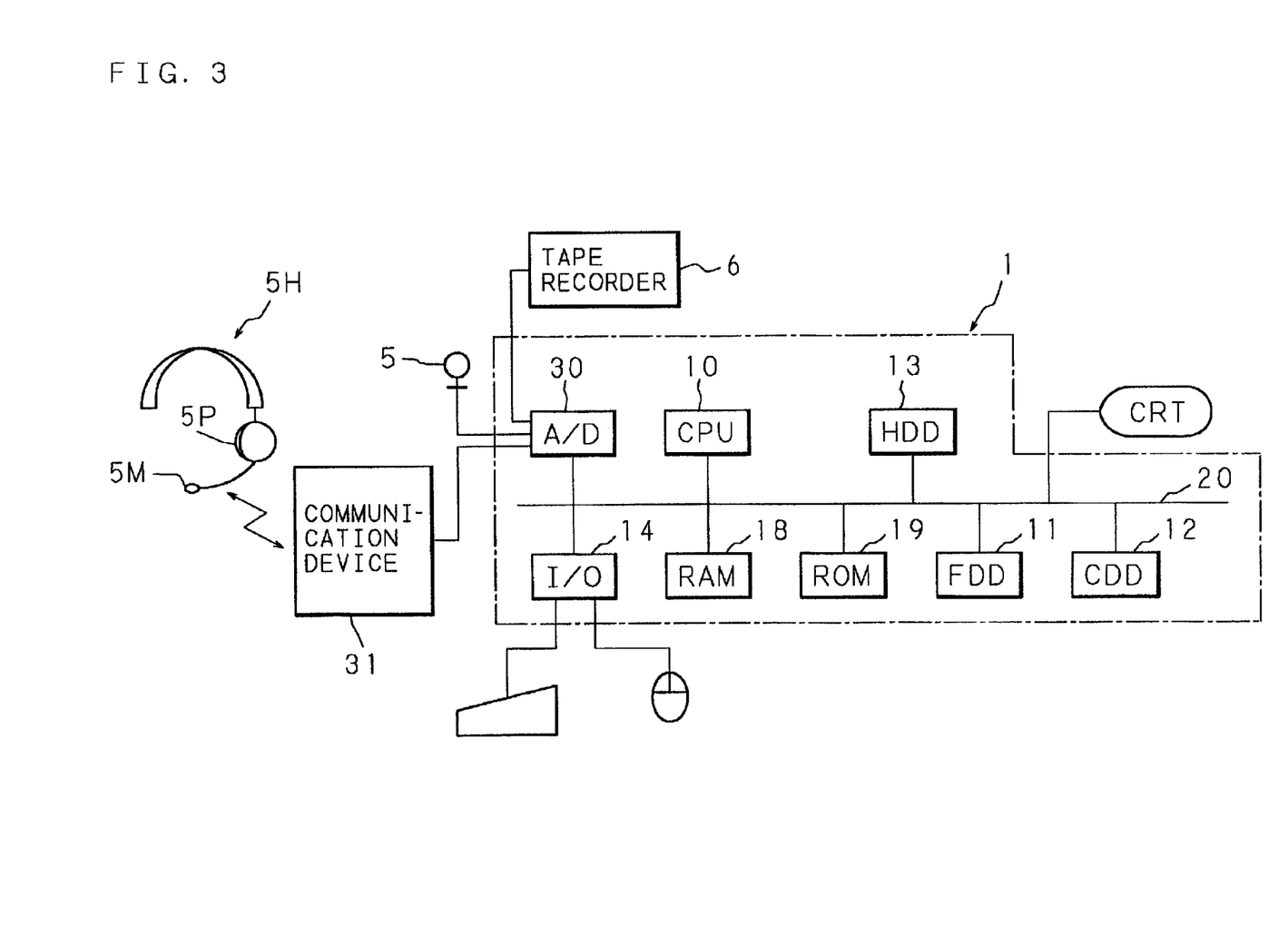
FIG. 3 is a block diagram illustrating an example of the internal constitution of the personal computer.

FIG. 3 is a block diagram showing an example of the internal constitution of the personal computer 1. Connected to the inside of the personal computer 1 are a CPU 10 as a main part, an I/O port 14, a RAM 18 and ROM 19 as storing means, an A/D converter 30 for converting an analog input signal into digital data, etc., in addition to the above-mentioned FDD 11, CDD 12, HDD 13 connected to a bus 20. Besides, connected to the outside of the personal computer 1 are the microphone 5, tape recorder 6 and communication device 31 via the above-mentioned A/D converter 30, and the keyboard and mouse via the I/O port 14. Further, the communication device 31 is connected to the above-mentioned headset 5H by radio or cable communication.

The program codes of the doze detecting program PG read from the flexible disk 11M by the FDD 11 or from the CD-ROM 12M by the CDD 12 are, for example, written and once stored in the HDD 13. When executing the doze detecting program PG, these program codes are read from the HDD 13 and transferred and stored into the RAM 18. However, it is also possible to execute the doze detecting program PG by reading the program codes of the doze detecting program PG from the FDD 11 or CDD 12 and transferring and storing them directly into the RAM 18.

In the case where the apparatus of the present invention is realized by such a personal computer 1, the microphone 5 and the microphone 5M of the headset 5H constitute voice inputting means together with the A/D converter 30 serving as analog/digital converting means, and the CPU 10 functions as Lyapunov exponent calculating means for calculating the Lyapunov exponents by performing chaos analysis of the digital data provided by the A/D converter 30, according to the chaos analyzing program PGC stored in the HDD 13, and also functions as judging means for judging a fatigue level and/or a dozing state from the calculation results.

Moreover, the CPU 10 functions as means for removing a voiceless part from the digital data provided by the A/D converter 30. Further, if the data length of the digital data after removing a voiceless part is less than a predetermined length, the CPU 10 also functions as means for generating digital data of the predetermined length by, for example, repeating the above digital data.

In addition, the HDD 13 functions as storing means for storing the calculation result of the Lyapunov exponent calculated by the CPU 10 as the Lyapunov exponent calculating means. Besides, it is, of course, possible to use the RAM 18 as storing means for storing the calculation result of the Lyapunov exponent, in place of the HDD 13 as the non-volatile storing means.

Figure 4:
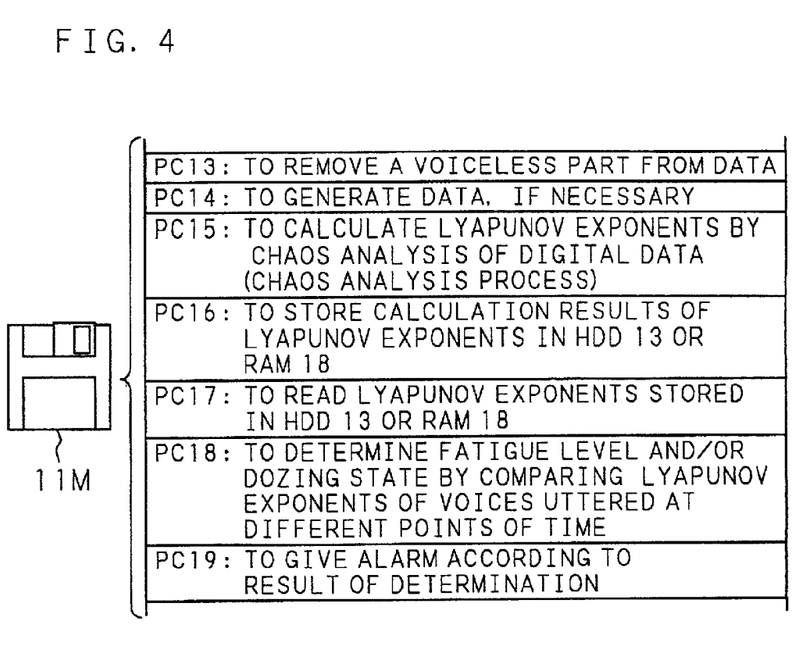
FIG. 4 is a schematic drawing showing the contents of a program recorded on a flexible disk as one example of a recording medium of the present invention.

FIG. 4 is a schematic drawing showing the contents of the doze detecting program PG recorded on the flexible disk 11M as one example of a recording medium of the present invention.

Recorded on the flexible disk 11M shown in FIG. 4 are the following program codes that constitute the doze detecting program PG for causing a computer to detect a person's fatigue level and/or dozing state by analyzing voices uttered by the same person at different points of time: namely, a program code (PC13) for causing the computer to remove a voiceless part from digital data; a program code (PC14) for causing the computer to generate data, if necessary, specifically, in the case where the data length of the digital data after removing the voiceless part is less than a predetermined length; a program code (PC15) of the chaos analyzing program PGC for causing the computer to calculate the Lyapunov exponents by chaos analysis of the digital data; a program code (PC16) for causing the computer to store the calculation results of the Lyapunov exponents in the HDD 13 or RAM 18; a program code (PC17) for causing the computer to read the Lyapunov exponents stored in the HDD 13 or RAM 18; a program code (PC18) for causing the computer to judge a fatigue level and/or a dozing state by comparing the Lyapunov exponents read from the HDD 13 or RAM 18; and a program code (PC19) for causing the computer to give an alarm according to the result of the judgment.

Figure 5:
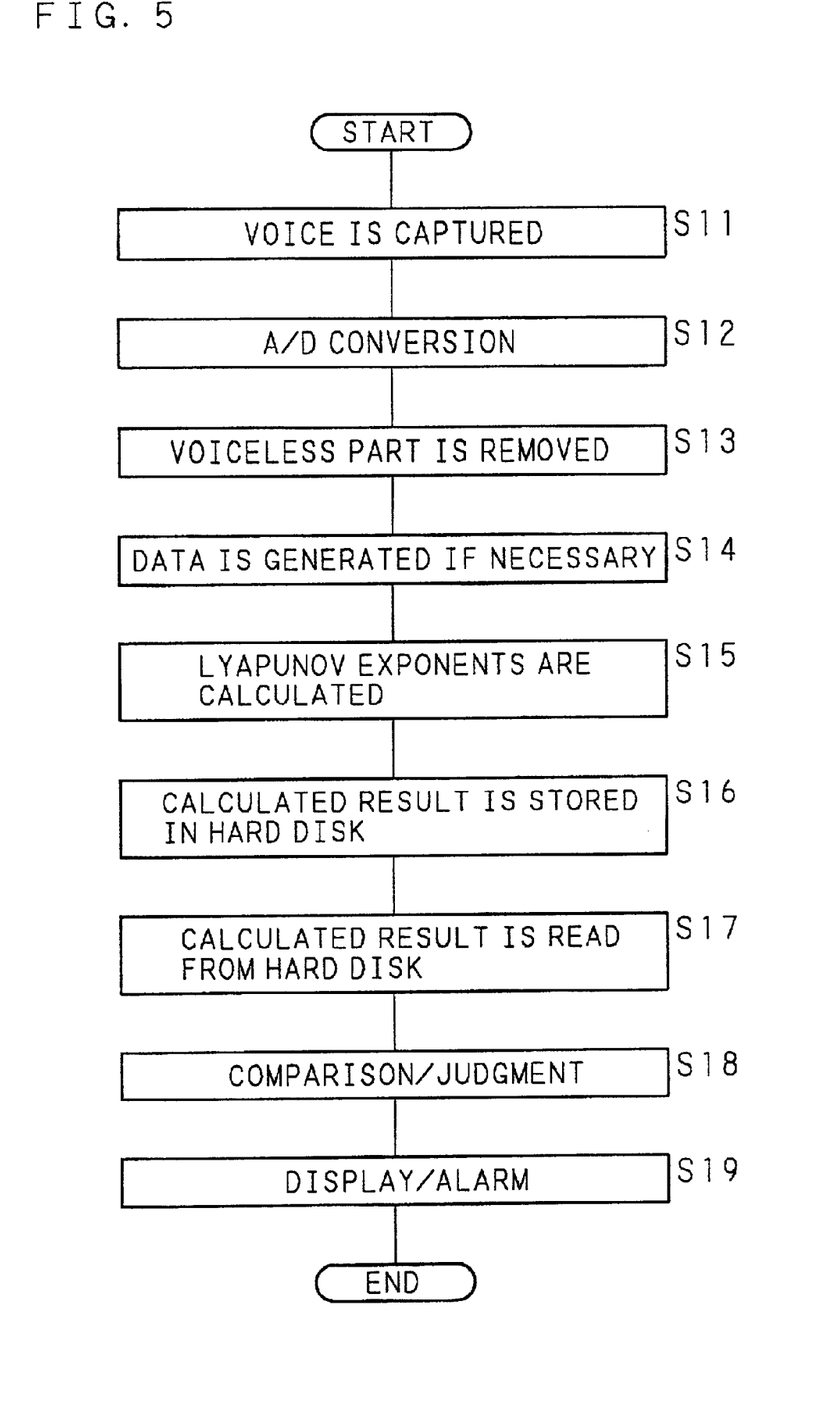
FIG. 5 is a flow chart showing the operation procedure of an apparatus for detecting fatigue and doze by voice of the present invention.

Referring to the flow chart shown in FIG. 5, the following description will explain an operation of the apparatus of the present invention which is realized by loading into the FDD 11 the flexible disk 11M as the recording medium on which the doze detecting program PG including the chaos analyzing program PGC as mentioned above is recorded and thereby installing the recorded doze detecting program PG in the personal computer 1.

At first, a voice of a person as the subject of a detection of a fatigue level or dozing state is captured by the apparatus of the present invention to obtain a sound signal (step S11). More specifically, the sound signal is inputted via the communication device 31, for example, the dispatching center of taxies, by inputting the voice from the microphone 5M of the headset 5H into which the subject inputs his/her voice directly.

At this time, however, the input of the voice is not necessarily performed by capturing the voice of the subject in real time, and may be performed by reproducing and inputting the sound signal recorded on the recording medium by a voice recorder of various types, for example, the tape recorder 6, or by inputting the sound signal through the microphone Sand storing it in advance.

Next, when the inputted sound signal is an analog signal, it is converted into a digital signal (step S12). More specifically, the A/D converter 30 samples the analog sound signal inputted through the microphone 5M into digital data at a sampling rate of about 10 kHz so that the sound signal can be processed by the computer.

Thereafter, pre-processing is performed. In this pre-processing, a process for removing a voiceless part from the digital data of the sound signal obtained by the A/D converter 30 is performed (step S13) and, in the case where the resultant digital data is less than a predetermined length (for example, a data length equivalent to one second) necessary for calculating the later-described Lyapunov exponent, a process for generating data is further performed (step S14). More specifically, this data generation process is a process performed when the data length of the digital data after removing the voiceless part is less than the predetermined length so as to generate data of the predetermined length by repeating the digital data a plurality of times.

Besides, as the pre-processing performed in steps S13 and S14, it is possible to perform another process, for example, a process for removing the consonant components by removing the high-frequency components by the Fourier transform or moving-average method.

Next, the Lyapunov exponents are calculated (step S15). The processing performed in step S15 calculates the Lyapunov exponents for chaos analysis of the data obtained by the pre-processing performed in steps S13 and S14. More specifically, the sound signal is four-to seven-dimensionally padded to generate an attractor. In this case, an appropriate padding delay time is not more than 10 ms, and more preferably about 1 ms. Moreover, for the evolution time necessary for calculating the Lyapunov exponents, a value equivalent to the delay time is given. Besides, in step S15, since the Lyapunov exponents are calculated substantially in real time, the data of the calculation results is suitably accumulated in the storing means, for example, in the HDD 13 (step S16).

However, it takes an extremely long time to precisely calculate the Lyapunov exponents. In this embodiment, therefore, the real time processing is substantially achieved by using an approximate calculating technique developed by "Sano and Sawada". Furthermore, in this embodiment, "SCATplus" available from Computer Convenience Inc. is used as software for performing this chaos analysis.

In the manner mentioned above, the calculation results of the Lyapunov exponents are sequentially accumulated in the HDD 13, and the past calculation results accumulated in the HDD 13 are read from the HDD 13 in suitable timing (step S17), and comparison and judgment are performed (step S18). Further, in this embodiment, while the calculated Lyapunov exponent is once stored in the HDD 13, it is also possible to store the Lyapunov exponent temporarily in the RAM 18 whenever the Lyapunov exponent is newly calculated and to compare it with the Lyapunov exponents which were calculated in the past and have been stored temporarily in the RAM 18.

Accordingly, in the case where time-series measurement is performed on the same subject, when the Lyapunov exponent shows a significant increasing tendency or when the Lyapunov exponent increases to about 1.15 in the relative value after the measuring start time, the apparatus of the present invention judges at that time that the subject's fatigue has accumulated to a certain extent or the subject has fallen into a dozing state. More specifically, since the calculation results in step S15 mentioned above are accumulated, for example, in the HDD 13, it is possible to detect whether the subject is fatigued, or in a dozing state, by comparing these time-series data.

Next, the result of the judgment in step S18 mentioned above is displayed on display means, for example, a CRT display, and an alarm is given to the subject directly or a manager, if necessary (step S19). This alarm may be given as a warning displayed on the CRT display of the personal computer, or may be given by sounding a bell or buzzer in close proximity to the subject or by calling attention by voice.

Moreover, in the apparatus of the present invention, since the calculation results of the Lyapunov exponents calculated in step S15 can be stored on the hard disk 13 as the non-volatile storing means beforehand, it is possible to capture the voices of a number of persons as the subjects in normal conditions as their reference values by the microphone 5 in advance. In such a case, therefore, immediately after starting the input of a current voice of a certain person, the relative value of the Lyapunov exponent with respect to that in normal conditions stored in the HDD 13 in step S18 can be calculated. It is thus possible to judge the current state of that person from the calculation result.

When the apparatus of the present invention is realized with the personal computer 1 in the manner mentioned above, the means for removing a voiceless part from digital data, the means for generating digital data of a predetermined length if the data length after removing the voiceless part from the digital data is less than the predetermined length, the Lyapunov exponent calculating means and the judging means are realized as software functions executed as steps S13, S14, S15 and S18, respectively, by the CPU 10 according to the doze detecting program PG installed on the hard disk 13.

Incidentally, while the above-described embodiment illustrates an example of the apparatus of the present invention realized by installing the doze detecting program PG recorded on the recording medium in the personal computer 1, needless to say, it is of course possible to realize the apparatus of the present invention as a dedicated apparatus, or to realize the functions, which are realized as software by the doze detecting program PG and chaos analyzing program PGC, by dedicated hardware.

Moreover, it is possible to record the Lyapunov exponents of individuals in normal conditions on ID cards or the like and to load the Lyapunov exponents in the personal computer 1 by a suitable reading device so as to use them as the reference values similar to those mentioned above.

Furthermore, while the above-described embodiment explains an example in which a voice is captured from the subject in real time to detect the subject's state, if the voice is still recorded on a recording medium, it is possible to analyze the voice afterward by reproducing the sound signal recorded on the recording medium with the use of a tape recorder or the like. Accordingly, for example, when an accident occurred, if the communication record over a certain period of time until the occurrence of the accident is present, there is a fear that the cause of the accident is found by reproducing the sound signals from a recording medium on which the communication record is recorded with a reproduction device such as the tape recorder 6 and analyzing them with the apparatus of the present invention.

Additionally, while the above-described embodiment illustrates an example in which the chaos analyzing program PGC is included in the doze detecting program PG, it is also possible to adopt a constitution in which chaos analysis is performed as a separate process because chaos analysis is an extremely complex process and requires an enormous amount of calculation.

As described above, according to the apparatus for detecting fatigue and doze by voice of the present invention, since voices uttered at different points of time are converted into digital data and subjected to chaos analysis so as to detect a fatigue level and/or a dozing state based on the Lyapunov exponents obtained as the results of the analysis, it is possible to detect a fatigue level and/or a dozing state without giving an excess of burden or an excess of stress to a person as the subject.

Moreover, when the voice inputting means is constructed by a microphone for inputting a voice as a sound signal and analog/digital converting means for converting a sound signal inputted to this microphone into digital data, since the voice of a person as the subject can be inputted through an ordinary microphone, it is possible to use a microphone belonging to headsets which are used daily by airplane pilots, air traffic controllers, drivers of public transport systems and so on, thereby requiring no extra sensors.

Furthermore, in the case where the Lyapunov exponent calculating means performs chaos analysis of the digital data of a sound signal recorded on a recording medium, it is possible to analyze the sound signal recorded on the recording medium afterward. Therefore, for example, when an accident occurred, it is possible to use the sound signals to investigate the cause of the accident by reproducing the record of communications with the voice of the party to the accident until the occurrence of the accident, stored on the recording medium.

Besides, in the case where a voiceless part has been removed from the digital data and the data length of the resultant data is less than a data length necessary for analysis, since a process for generating data is performed, data necessary and sufficient for analysis is inputted.

Additionally, by storing data obtained by analysis of voices of a plurality of persons as the subjects in normal conditions as the reference values of the individuals in advance, it is possible to perform detection on a number of persons as the subjects and to perform prompt and accurate detection.

Further, with a recording medium of the present invention, by causing a general-purpose computer to read the recording medium, it is possible to realize an apparatus for detecting fatigue and doze by voice as described above with the general-purpose computer.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. An apparatus for detecting fatigue and doze by voice, comprising:

a controller capable of performing the following operations:

calculating Lyapunov exponents by chaos analysis of digital data of voices;

judging a fatigue level and/or a dozing state by comparing the calculated Lyapunov exponents of voices uttered at different points of time; and a storing device for storing calculation results obtained by the operation of calculating the Lyapunov exponents, wherein said controller is coupled to said storing device and further capable of performing the operation of comparing the Lyapunov exponents of voices uttered at different points of time based on the calculation results, which were obtained in advance by the operation of calculating the Lyapunov exponents and are stored in said storing device, during the judging operation.

2. The apparatus for detecting fatigue and doze by voice as set forth in claim 1, further comprising:

a microphone for inputting a voice as a sound signal and an analog/digital converting device for converting the sound signal inputted to said microphone into digital data.

3. The apparatus for detecting fatigue and doze by voice as set forth in claim 1, wherein the calculation of the Lyapunov exponents by said controller is performed by chaos analysis of digital data of sound signals recorded on a recording medium.

4. The apparatus for detecting fatigue and doze by voice as set forth in claim 1, wherein said controller is further capable of performing the operation of removing a voiceless part from the digital data prior to the calculation of the Lyapunov exponents.

5. The apparatus for detecting fatigue and doze by voice as set forth in claim 4, wherein said controller is further capable of performing the operation of generating digital data of a predetermined length by data based on said digital data, in the case where a data length of said digital data, after removing the voiceless part, is less than the predetermined length, prior to the calculation of the Lyapunov exponents.

6. A computer readable recording medium on which a program for causing a computer to detect a fatigue level and/or a dozing state by analysis of voices uttered at different points of time is recorded, including:

program code means for causing a computer to remove a voiceless part from digital data of voices;

program code means for causing a computer to generate digital data of a predetermined length from data based on loaded digital data, in the case where a data length after removing a voiceless part from said loaded digital data is less than the predetermined length;

program code means for causing a computer to give the loaded data to a chaos analyzing process for calculating Lyapunov exponents by chaos analysis;

program code means for causing a computer to store calculation results of the Lyapunov exponents calculated by said chaos analyzing process;

program code means for causing a computer to read the stored Lyapunov exponents; and program code means for causing the computer to judge a fatigue level and/or a dozing state by comparing the read Lyapunov exponents of voices uttered at different points of time.

* * * * *